(12) United States Patent
Tamura

(10) Patent No.: US 11,284,000 B2
(45) Date of Patent: Mar. 22, 2022

(54) MEDICAL OBSERVATION DEVICE, MEDICAL OBSERVATION SYSTEM, AND IMAGE SHAKE CORRECTION METHOD

(71) Applicant: Sony Olympus Medical Solutions Inc., Tokyo (JP)

(72) Inventor: Shigeru Tamura, Tokyo (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 0 days.

(21) Appl. No.: 16/553,174

(22) Filed: Aug. 28, 2019

(65) Prior Publication Data

US 2019/0394400 A1 Dec. 26, 2019

Related U.S. Application Data

(63) Continuation of application No. 15/398,157, filed on Jan. 4, 2017, now abandoned.

(30) Foreign Application Priority Data

Jan. 19, 2016 (JP) .................................. 2016-007621

(51) Int. Cl.
*A61B 90/20* (2016.01)
*A61B 90/25* (2016.01)
(Continued)

(52) U.S. Cl.
CPC ......... *H04N 5/23287* (2013.01); *A61B 1/045* (2013.01); *A61B 1/05* (2013.01);
(Continued)

(58) Field of Classification Search
CPC ....... A61B 1/00149; A61B 1/046; A61B 1/05; A61B 2034/2048; A61B 2090/504;
(Continued)

(56) References Cited

U.S. PATENT DOCUMENTS 2,136,759 A * 11/1938 Ryan ........................ G01H 9/00
73/653
6,246,054 B1 * 6/2001 Toda ....................... G01Q 60/38
850/1

(Continued)

FOREIGN PATENT DOCUMENTS

DE 10133671 A1 * 1/2002 ............. A61B 90/36
JP 8-5922 A 1/1996
(Continued)

OTHER PUBLICATIONS

Japanese Office Action dated Oct. 1, 2019, issued in corresponding Japanese Patent Application No. 2016-007621.

*Primary Examiner* — Reza Aghevli
(74) *Attorney, Agent, or Firm* — Xsensus LLP

(57) ABSTRACT

There is provided a medical observation device, including: an observation unit configured to perform magnified observation of a surgical site; a vibration sensor that detects a vibration of the observation unit; a support unit that supports the observation unit; and a control unit that conducts an image shake correction that corrects a shake in an image observed by the observation unit, based on a detection value from the vibration sensor.

16 Claims, 6 Drawing Sheets

(51) Int. Cl.
| | |
|---|---|
| *A61B 1/045* | (2006.01) |
| *A61B 1/24* | (2006.01) |
| *A61B 1/00* | (2006.01) |
| *G02B 23/24* | (2006.01) |
| *G02B 27/64* | (2006.01) |
| *G02B 7/00* | (2021.01) |
| *H04N 5/232* | (2006.01) |
| *A61B 90/00* | (2016.01) |
| *A61B 1/05* | (2006.01) |
| *H04N 5/225* | (2006.01) |
| *A61B 90/50* | (2016.01) |
| *A61B 34/20* | (2016.01) |

(52) U.S. Cl.
CPC .............. *A61B 90/20* (2016.02); *A61B 90/25* (2016.02); *A61B 90/361* (2016.02); *G02B 23/2407* (2013.01); *G02B 23/2484* (2013.01); *G02B 27/646* (2013.01); *H04N 5/2256* (2013.01); *H04N 5/23258* (2013.01); *H04N 5/23267* (2013.01); *A61B 1/00149* (2013.01); *A61B 2034/2048* (2016.02); *A61B 2090/504* (2016.02); *A61B 2090/506* (2016.02); *G02B 7/001* (2013.01); *H04N 2005/2255* (2013.01)

(58) Field of Classification Search
CPC ... A61B 2090/506; A61B 90/20; A61B 90/25; A61B 90/361; G02B 23/2407; G02B 23/2484; G02B 27/646; G02B 7/001; H04N 2005/2255; H04N 5/2256; H04N 5/23258; H04N 5/23267; H04N 5/23287
See application file for complete search history.

(56) References Cited

U.S. PATENT DOCUMENTS

| | | | |
|---|---|---|---|
| 6,392,795 B2* | 5/2002 | Okada .................. | G02B 21/24 359/368 |
| 6,615,811 B1 | 9/2003 | Butler, Jr. et al. | |
| 6,628,457 B2* | 9/2003 | Ito ........................ | A61B 90/25 359/368 |
| 6,734,901 B1* | 5/2004 | Kudo .................. | H04N 5/23248 348/208.1 |
| 7,820,958 B2* | 10/2010 | Ishihara ............. | G01N 21/6445 250/234 |
| 8,582,202 B2* | 11/2013 | Terada ................ | G02B 21/0016 359/368 |
| 8,615,811 B2* | 12/2013 | Shigeno .............. | B82Y 35/00 850/5 |
| 9,539,059 B2* | 1/2017 | Fukushima ........... | G05B 15/02 |
| 2001/0024320 A1* | 9/2001 | Okada .................. | G02B 21/24 359/368 |
| 2002/0085273 A1* | 7/2002 | Ito ...................... | G02B 27/646 359/369 |
| 2004/0160667 A1* | 8/2004 | Sander .................. | G02B 7/001 359/368 |
| 2005/0129392 A1* | 6/2005 | Shinohara ............ | G03B 5/00 396/50 |
| 2005/0167550 A1* | 8/2005 | Poxleitner ............ | F16M 11/10 248/125.2 |
| 2006/0018647 A1* | 1/2006 | Iwanaga ............. | H04N 5/2254 396/55 |
| 2008/0149832 A1* | 6/2008 | Zorn .................... | G01Q 10/045 250/311 |
| 2008/0278781 A1* | 11/2008 | Sander .................. | G02B 26/0833 359/198.1 |
| 2009/0015894 A1* | 1/2009 | Rosman .............. | G02B 26/103 359/199.1 |
| 2009/0020666 A1* | 1/2009 | Brenner ................ | A61B 90/50 248/176.1 |
| 2009/0255016 A1* | 10/2009 | Wakiyama ............ | G01Q 70/04 850/33 |
| 2010/0020184 A1* | 1/2010 | Kurosawa ............ | H04N 5/2253 348/208.11 |
| 2010/0211225 A1* | 8/2010 | Heiland ................ | G03F 7/709 700/280 |
| 2011/0109968 A1* | 5/2011 | Park .................... | H04N 5/2253 359/554 |
| 2011/0113515 A1* | 5/2011 | Ito ........................ | G01Q 20/02 850/6 |
| 2011/0130679 A1* | 6/2011 | Breslauer ............ | A61B 10/0096 600/566 |
| 2011/0204229 A1* | 8/2011 | Schamber ............ | H01J 37/28 250/311 |
| 2012/0026312 A1* | 2/2012 | Sander ................ | G02B 21/0012 348/79 |
| 2012/0099201 A1* | 4/2012 | Chan .................... | G02B 7/04 359/557 |
| 2013/0053657 A1* | 2/2013 | Ziarno ................ | A61B 5/14539 600/304 |
| 2013/0120833 A1* | 5/2013 | Hirano .................. | G02B 21/06 359/385 |
| 2013/0120834 A1* | 5/2013 | Sukekawa ............ | G02B 21/08 359/390 |
| 2014/0137300 A1* | 5/2014 | Moon .................. | G01Q 60/24 850/1 |
| 2014/0160566 A1* | 6/2014 | Shihoh ................ | G03B 5/00 359/557 |
| 2014/0362242 A1* | 12/2014 | Takizawa ............ | H04N 5/2254 348/208.11 |
| 2014/0375829 A1* | 12/2014 | Nishihara .......... | H04N 5/23287 348/208.7 |
| 2015/0042870 A1 | 2/2015 | Chan et al. | |
| 2015/0103234 A1* | 4/2015 | Takei ................ | H04N 5/232123 348/357 |
| 2015/0198797 A1* | 7/2015 | Andre .................... | G02B 21/16 348/80 |
| 2015/0219878 A1* | 8/2015 | Kim .................... | G02B 27/646 348/345 |
| 2015/0250547 A1* | 9/2015 | Fukushima ............ | B25J 9/1697 606/130 |
| 2015/0313679 A1* | 11/2015 | Fukushima ........... | A61B 34/30 600/102 |
| 2016/0235340 A1* | 8/2016 | Sidar ...................... | A61B 5/065 |
| 2016/0246041 A1* | 8/2016 | Rappel ................ | G02B 21/368 |
| 2016/0266365 A1* | 9/2016 | Nolte .................. | G02B 21/365 |
| 2016/0295115 A1* | 10/2016 | Hjelmstrom ........ | H04N 5/23212 |
| 2016/0327806 A1* | 11/2016 | Kasamatsu .......... | G02B 27/646 |
| 2016/0360111 A1* | 12/2016 | Thivent ................ | H04N 5/23287 |
| 2017/0007336 A1* | 1/2017 | Tsuboi .................. | A61B 34/30 |
| 2017/0007342 A1* | 1/2017 | Kasai .................... | A61B 90/361 |
| 2017/0017058 A1* | 1/2017 | Sumioka ................ | G03B 5/00 |
| 2017/0041576 A1* | 2/2017 | Kobayashi ............ | H04N 5/2256 |
| 2017/0066131 A1* | 3/2017 | Kamikawa ............ | B25J 9/1697 |
| 2017/0079729 A1* | 3/2017 | Fukushima ............ | G05B 15/02 |
| 2017/0080574 A1* | 3/2017 | Kuroda ................ | A61B 34/74 |
| 2017/0163176 A1* | 6/2017 | Tsuchiya .............. | G02B 21/26 |
| 2017/0176768 A1* | 6/2017 | Kim .................... | G02B 27/646 |
| 2018/0235716 A1* | 8/2018 | Hane .................. | A61B 1/00009 |
| 2019/0179409 A1* | 6/2019 | Jones .................... | G02B 27/0093 |

FOREIGN PATENT DOCUMENTS

| | | |
|---|---|---|
| JP | 2001-25472 A | 1/2001 |
| JP | 2002-14287 A | 1/2002 |
| JP | 2002-90650 A | 3/2002 |
| JP | 2005-198700 A | 7/2005 |
| JP | 2006-201592 A | 8/2006 |
| JP | 2009-180828 A | 8/2009 |
| WO | WO-2008156038 A1 * | 12/2008 ............. G02B 7/022 |

* cited by examiner

MEDICAL OBSERVATION DEVICE, MEDICAL OBSERVATION SYSTEM, AND IMAGE SHAKE CORRECTION METHOD

CROSS REFERENCE TO RELATED APPLICATIONS

This application is a continuation of U.S. application Ser. No. 15/398,157, filed Jan. 4, 2017, and claims the benefit of Japanese Priority Patent Application No. 2016-007621, filed Jan. 19, 2016, the entire contents of each are incorporated herein by reference.

BACKGROUND

The present disclosure relates to a medical observation device, a medical observation system, and an image shake correction method.

In surgical operations, a technique is used in which surgery is performed while observing the surgical site with observation equipment (hereinafter also called the observation unit) enabling magnified observation of the surgical site, such as a microscope. In such situations, a medical observation device that holds the observation unit with an arm unit (support unit) is used to move and lock the position and orientation of the observation unit with high precision.

At this point, in a medical observation device, the observation unit may vibrate in some cases, because of factors such as the footsteps of medical staff moving inside the operating room, for example. Since such vibrations induce shaking in the observation image (image shake) during magnified observation, in some cases work may not be performed until the shaking subsides, thereby increasing the mental strain on the surgeon, and also lowering the efficiency of surgery.

Accordingly, in observation equipment for providing magnified observation of a target of observation, technology for obtaining a. stable observation image with suppressed vibration is being developed. For example, JP H8-5922A discloses technology in which a microscope is equipped with an acceleration sensor for detecting vibration, and by driving the objective lens at the inverse phase of the vibration detected by the acceleration sensor, enables a stable observation image to be obtained.

SUMMARY

However, the technology described in JP H8-5922A does not target a microscope unit supported by an arm unit, and in addition, does not presuppose the application of observing a surgical site during surgery. In this way, the technology described in JP H8-5922A is not necessarily suited to a medical observation device.

Accordingly, the present disclosure proposes a new and improved medical observation device, medical observation system, and image shake correction method capable of obtaining a stable observation image less affected by vibration.

According to an embodiment of the present disclosure, there is provided a medical observation device, including: an observation unit configured to perform magnified observation of a surgical site; a vibration sensor that detects a vibration of the observation unit; a support unit that supports the observation unit; and a control unit that conducts an image shake correction that corrects a shake in an image observed by the observation unit, based on a detection value from the vibration sensor.

According to an embodiment of the present disclosure, there is provided a medical observation system, including: a medical observation device including an imaging unit that captures an image of a surgical site, a vibration sensor that detects a vibration of the imaging unit, a support unit that supports the imaging unit, and a control unit that conducts an image shake correction that corrects a shake in an image captured by the imaging unit, based on a detection value from the vibration sensor; and a display device that displays an image subjected to the image shake correction by the medical observation device.

According to an embodiment of the present disclosure, there is provided an image shake correction method conducted in a medical observation device that includes an observation unit configured to perform magnified observation of a surgical site, a vibration sensor that detects a vibration of the observation unit, and a support unit that supports the observation unit, the image shake correction method including: conducting an image shake correction that corrects a shake in an image observed by the observation unit, based on a detection value from the vibration sensor.

According to an embodiment of the present disclosure, vibration of the observation unit is detected by a vibration sensor, and based on the detection value, image shake correction that corrects shake in the image obtained by the observation unit is conducted. Consequently, it becomes possible to obtain a stable observation image less affected by vibration. Thus, it becomes possible to reduce the mental strain on the surgeon during surgery, and also help surgery proceed smoothly.

According to an embodiment of the present disclosure as described above, it becomes possible to obtain a stable observation image less affected by vibration. Note that the effects described above are not necessarily limitative. With or in the place of the above effects, there may be achieved any one of the effects described in this specification or other effects that may be grasped from this specification.

DETAILED DESCRIPTION OF THE EMBODIMENT(S)

Figure 1:
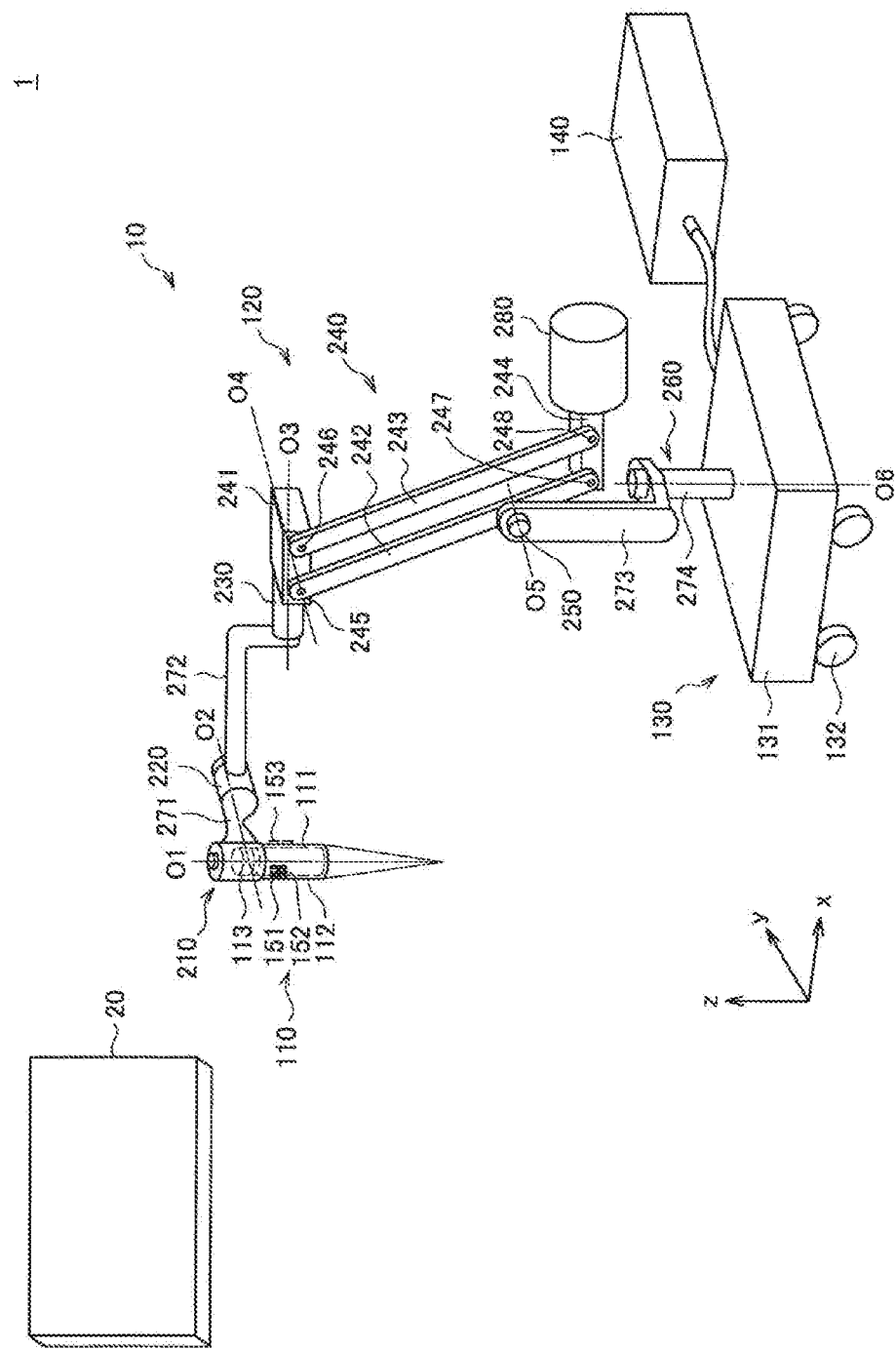
FIG. 1 is a diagram illustrating an example configuration of an observation system according an embodiment.

Hereinafter, (a) preferred embodiment(s) of the present disclosure will be described in detail with reference to the appended drawings. In this specification and the appended drawings, structural elements that have substantially the same function and structure are denoted with the same reference numerals, and repeated explanation of these structural elements is omitted.

Hereinafter, the description will proceed in the following order.

1. Configuration of Observation Device
2. Details of IMAGE SHAKE CORRECTION PROCESS
3. Image Shake Correction Method
4. Supplemental Remarks Note that in the following, the user who performs various operations on an observation device according to an embodiment of the present disclosure is designated the surgeon for the sake of convenience. However, this designation does not limit the user who uses the observation device, and the various operation on the observation device may also be executed by any user, such as another member of the medical staff.

1. Configuration of Observation Device

With reference to FIG. 1, a configuration of an observation system according to a preferred embodiment of the present disclosure will be described, and in addition, a configuration of an observation device constituting such an observation system will be described. FIG. 1 is a diagram illustrating an example configuration of an observation system according the present embodiment.

An observation system 1 according to the present embodiment is a medical observation device used for medical procedures such as surgeries and examinations. Referring to FIG. 1, the observation system 1 according to the present embodiment is made up of an observation device 10, which is equipped with a microscope unit 110 and which captures images of the surgical site of a patient with the microscope unit 110, and a display device 20, which displays images of the surgical site captured by the observation device 10 (still images and moving images). During a surgery or an examination, the surgeon observes the surgical site and performs various treatments on the surgical site while referring to images captured by the observation device 10 and displayed on the display device 20.

Display Device

As discussed above, the display device 20 displays images of the patient's surgical site captured by the observation device 10. The display device 20 is installed in a location visible to the surgeon inside the operating room, such as on a wall of the operating room, for example. The type of the display device 20 is not particularly limited, and any of various known types of display devices may be used as the display device 20, such as a cathode ray tube (CRT) display device, a liquid crystal display device, a plasma display device, or an electroluminescence (EL) display device. Additionally, the display device 20 is not necessarily required to be installed inside the operating room, and may also be mounted onboard a device used by being worn on the surgeon's body, such as a head-mounted display (HMD) or an eyeglasses-type wearable device.

Observation Device

The observation device 10 is equipped with a microscope unit 110 for performing magnified observation of the patient's surgical site, a support unit 120 (arm unit 120) that holds the microscope unit 110, a base unit 130 to which one end of the support unit 120 is connected and which supports the microscope unit 110 and the support unit 120, and a control device 140 that controls the operation of the observation device 10.

Base Unit

The base unit 130 supports the microscope unit 110 and the support unit 120. The base unit 130 includes a platform 131 having a planar shape, and multiple casters 132 provided on the bottom face of the platform 131. One end of the support unit 120 is connected to the top face of the platform 131, while the microscope unit 110 is connected to the other end of the support unit 120 extending from the platform 131 (the leading end). Also, the observation device 10 is in contact with the floor through the casters 132, and is configured to be movable across the floor by the casters 132.

Note that in the following description, the direction perpendicular to the floor on which the observation device 10 is installed is defined to be the z-axis direction. The z-axis direction is also called the up-and-down direction or the vertical direction. Additionally, the two mutually orthogonal directions to the z-axis direction are defined to be the x-axis direction and the y-axis direction. The direction parallel to the x-y plane is also called the horizontal direction.

Microscope Unit

The microscope unit 110 is made up of a microscope body for performing magnified observation of the patient's surgical site. In the illustrated example, the optical axis direction of the microscope unit 110 is approximately aligned with the z-axis direction. The microscope unit 110 has a configuration corresponding to a microscope of the electronic imaging type, and is made up of a barrel unit 112 having an approximately cylindrical shape, and an imaging unit 111 provided inside the barrel unit 112. Additionally, the imaging unit 111 is made up of an optical system such as an objective lens and a zoom lens, and an image sensor that captures an image of a subject (namely, the surgical site) with light passing through the optical system. Also, in the present embodiment, the microscope unit 110 is provided with a vibration sensor 113 for detecting vibration of the imaging unit 111.

The aperture on the bottom end of the barrel unit 112 is provided with a cover glass for protecting the imaging unit 111. A light source is also provided inside the barrel unit 112, and during image capture, the subject is irradiated with illuminating light radiating from the light source through the cover glass. Of this illuminating light, the light reflecting back from the subject (observation light) is incident on the imaging unit 111 via the cover glass, and as a result, a signal corresponding to an image of the surgical site (image signal) is acquired by the imaging unit 111.

For the imaging unit 111, it is sufficient to apply a configuration used in any of various known types of electronic imaging microscope units, and for this reason a detailed description thereof will be reduced or omitted herein. For example, any of various known types of image sensors may be applied as the image sensor of the imaging unit 111, such as a charge-coupled device (CCD) sensor or a complementary metal-oxide-semiconductor (CMOS) sensor. Additionally, the imaging unit 111 may also be configured as a stereo camera equipped with a pair of image sensors. Also, any of various known types of configurations may be applied to the optical system of the imaging unit 111. Furthermore, any of various types of functions typically provided in electronic imaging microscope units, such as an autofocus (AF) function and an optical zoom function, may be provided onboard the imaging unit 111.

The vibration sensor 113 is a sensor that detects vibration of the imaging unit 111 (such as the vibration direction, amplitude, and frequency, for example). Any of various known types of sensors typically used to detect vibration, such as an acceleration sensor or a gyro sensor, may be used as the vibration sensor 113. However, as discussed later, in the present embodiment, since an image shake correction process that corrects shake in an image captured by the imaging unit 111 (in other words, shake in the observation image) is conducted based on a detection value from the vibration sensor 113, a sensor able to detect at least vibration in the plane parallel to the photosensitive face of the image sensor is used as the vibration sensor 113. Also, the vibration sensor 113 preferably is installed near the imaging unit 111 to enable more precise detection of vibration of the imaging unit 111. Furthermore, preferably, the vibration sensor 113 is also comparatively compact so that the microscope unit 110 is more compact.

The image signal acquired by the microscope unit 110 is transmitted to the control device 140. In the control device 140, various types of image processing are performed on the image signal, such as gamma correction, white balance adjustment, magnification and pixel interpolation related to the electronic zoom function. For the image processing, various types of image processing typically performed to display images may be performed. Additionally, in the present embodiment, a detection value from the vibration sensor 113 is also transmitted to the control device 140. Furthermore, the control device 140 includes a function of deciding a vibration mode of the imaging unit 111, and the control device 140 executes an image shake correction process based on the decided vibration mode and the detection value. Note that the image shake correction process will be described in further detail in the later section (2. Details of image shake correction process). An image signal that has been subjected to the above image processing as well as image shake correction is transmitted to the display device 20 provided in the operating room, and an image of the surgical site is displayed on e display device 20, appropriately magnified at a desired magnification by an optical zoom function and/or an electronic zoom function, for example. Note that the communication between the control device 140 and the display device 20 may be realized by any of various known wired or wireless methods.

Note that a processing circuit for performing the above image processing may be provided in the microscope unit 110, and the above image processing may be performed by the processing circuit of the microscope unit 110, without being performed by the control device 140. In this case, image information after suitable image processing has been performed in the processing circuit onboard the Microscope unit 110 may be transmitted from the microscope unit 110 to the display device 20 provided in the operating room. Also, in this case, the communication between the microscope unit 110 and the display device 20 may be realized by any of various known wired or wireless methods.

The microscope unit 110 is provided with various types of switches for controlling the operation of the microscope unit 110. For example, the microscope unit 110 is provided with a zoom switch 151 (zoom SW 151) and a focus switch 152 (focus SW 152) for adjusting the image capture parameters of the microscope unit 110, as well as an operating mode toggle switch 153 (operation mode toggle SW 153) for toggling the operating mode of the support unit 120.

The surgeon, by operating the zoom SW 151 and the focus SW 152, is able to adjust the magnification and the focal length of the microscope unit 110, respectively. Also, by operating the operating mode toggle SW 153, the surgeon is able to toggle the operating mode of the support unit 120 between a locked mode and a free mode.

Herein, the locked mode is an operating mode in which the position and the orientation of the microscope unit 110 are locked by using a brake to restrain rotation about each rotation axis provided in the support 120. The free mode is an operating mode in which the brake is released, thereby allowing free rotation about each rotation a is provided in the support unit 120, and enabling the surgeon to adjust the position and the orientation of the microscope unit 110 with direct operations. Herein, direct operations mean operations in which the surgeon grips the microscope unit 110 with his or her hand, for example, and directly moves the microscope unit 110. For example, the operating mode of the support unit 120 becomes the free mode while the surgeon is pressing the operating mode toggle SW 153, and the operating mode of the support unit 120 becomes the locked mode while the surgeon releases his or her hand from the operating mode toggle SW 153.

Note that these switches are not necessarily required to be provided on the microscope unit 110. In the present embodiment, it is sufficient for the observation device 10 to be provided with a mechanism for accepting operating input having functions similar to these switches, and the specific configuration of such a mechanism is not limited. For example, these switches may also be provided on another section of the observation device 10. As another example, an input device such as a remote control may be used, and commands corresponding to these switches may be input into the observation device 10 remotely.

Also, although the barrel unit 112 of the microscope unit 110 is illustrated as a simple cylindrically-shaped member in FIG. 1 for the sake of simplicity, the barrel unit 112 may also be provided with a grip unit gripped by the surgeon. Such a grip unit may be realized by having a structure such as a handle to be gripped by the surgeon be formed around the outer circumference of the barrel unit 112. Alternatively, such a grip unit may be realized by having the shape of the barrel unit 112 be formed into a shape that is gripped easily by the surgeon. For example, when in the free mode, operations of moving the microscope unit 110 with the surgeon gripping the barrel unit 112 directly in hand may be anticipated. At this point, since the surgeon performs an operation of moving the microscope unit 110 while pressing the operating mode toggle SW 153, the shape of the barrel unit 112 and the placement of the operating mode toggle SW 153 may be decided appropriately with consideration for operability by the surgeon while in the free mode. In addition, the placement of the zoom SW 151 and the focus SW 152 may be decided appropriately with similar consideration for operability by the surgeon.

Control Device

The control device 140 is made up of a processor, such as a central processing unit (CPU) or a digital signal processor (DSP), for example, or a control board on which these processors are mounted together with components such as memory. By executing computational processing according to a certain program, the control device 130 controls the operation of the observation device 10.

For example, the control device 140 includes a function of toggling the operating mode of the support unit 120 discussed earlier by controlling the driving of the brake provided in each joint unit of the support unit 120 in response to operating input performed by the surgeon via the above operating mode toggle SW 153. As another example, the control device 140 includes a function of appropriately driving the optical system in the imaging unit 111 of the microscope unit 110 to adjust the magnification and the focal length of the microscope unit 110 in response to operating input performed by the surgeon via the above zoom SW 151 and focus SW 152. In addition, the control device 140 includes a function of performing various types of image processing on an image signal acquired by the microscope unit 110, and causing the display device 20 to display the processed image signal. At this point, in the present embodiment, an image shake correction process is conducted by the control device 140, and an image with suppressed image shake is displayed on the display device 20.

Note that in the illustrated example, the control device 140 is provided as a separate configuration from the microscope unit 110, the support unit 120, and the base unit 130, and is connected to the base unit 130 by a cable. However, the present embodiment is not limited to such an example. For example, a processor, a control board, or the like that realizes functions similar to the control device 140 may also be disposed inside the base unit 130. Additionally, by incorporating a processor, a control board, or the like that realizes functions similar to the control device 140 into the microscope unit 110 internally, the control device 140 and the microscope unit 110 may be configured in an integrated manner.

Support Unit

The support unit 120 holds the microscope unit 110, and moves the microscope unit 110 three-dimensionally while also locking the position and the orientation of the microscope unit 110 after moving. In the present embodiment, the support unit 120 is configured as a balance arm having six degrees of freedom. However, the present embodiment is not limited to such an example, and the support unit 120 may also be configured to have a different number of degrees of freedom, insofar as the support unit 120 is configured sufficiently to allow the microscope unit 110 to move appropriately according to the intended purpose.

The support unit 120 is provided with six rotation axes corresponding to the six degrees of freedom (first axis $O_1$, second axis $O_2$, third axis $O_3$, fourth axis $O_4$, fifth axis $O_5$, and sixth axis $O_6$. In the following description, for the sake of convenience, the members constituting each rotation axis will be referred to collectively as the rotation axis unit. For example, the rotation axis unit may be made up of components such as a bearing, a shaft rotatably inserted into the bearing, and a brake that restrains rotation about the rotation axis. The parallelogram link mechanism 240 discussed later may also be considered to be one of the rotation axis units.

The support unit 120 is made up of a first rotation axis unit 210, a second rotation axis unit 220, a third rotation axis unit 230, a fourth rotation axis unit 240, a fifth rotation axis unit 250, and a sixth rotation axis unit 260 corresponding to each rotation axis, a first arm unit 271, a second arm unit 272, a third arm unit 273, and a fourth arm unit 274 rotatably connected to each other by the first rotation axis unit 210 to the sixth rotation axis unit 260, and a counterweight 280 for maintaining equilibrium of the moment of the microscope unit 110 and the support unit 120 as a whole. Note that the fourth rotation axis unit 240 corresponds to the parallelogram link mechanism 240.

Note that in the following description, when describing the configuration of the support unit 120, the side on which the microscope unit 110 is provided may also be called the leading end side or the leading end unit, while the side near the base unit 130 may also be called the base end side or the base end unit.

The first rotation axis unit 210 has an approximately cylindrical shape, and is connected to the base end unit of the barrel unit 112 of the microscope unit 110 so that the central axis is approximately aligned with the central axis of the barrel unit 112 of the microscope unit 110. The first rotation axis unit 210 rotatably supports the microscope unit 110, with the rotation axis direction (first axis $O_1$ direction) being a direction approximately aligned with the optical axis of the microscope unit 110. In the example illustrated in FIG. 1, the first axis $O_1$ is provided as a rotation axis approximately parallel to the z-axis. By having the microscope unit 110 rotate about the first axis $O_1$ by the first rotation axis unit 210, the direction of images captured by the microscope unit 110 is adjusted.

Note that in the illustrated example, part of the imaging unit 111 of the microscope unit 110 is stored inside the cylindrical housing constituting the first rotation axis unit 210. In other words, the microscope unit 110 and the first rotation axis unit 210 are configured as an integrated member. However, the present embodiment is not limited to such an example, and the first rotation axis unit 210 and the microscope unit 110 may also be configured as mutually separate members.

The leading end of the first arm unit 271 extending in a direction approximately perpendicular to the first axis $O_1$ is connected to the first rotation axis unit 210. Also, at the base end of the first arm unit 271, there is provided the second rotation axis unit 220 that rotatably supports the first arm unit 271, with the rotation axis direction (second axis $O_2$ direction) being a direction approximately parallel to the extension direction of the first arm unit 271. The second axis $O_2$ is a rotation axis approximately perpendicular to the first axis $O_1$, and in the example illustrated in FIG. 1, is provided as a rotation axis approximately parallel to the y-axis. By having the microscope unit 110 and the first arm unit 271 rotate about the second axis $O_2$ as a rotation axis by the second rotation axis unit 220, the position in the x-axis direction of the microscope unit 110 is adjusted.

The leading end of the second arm unit 272 extending in a direction approximately perpendicular to both the first axis $O_1$ and the second axis $O_2$ is connected to the second rotation axis unit 220. The base end side of the second arm unit 272 is curved in an L-shape, and at the position corresponding to the curved short side, there is provided the third rotation axis unit 230 that rotatably supports the second arm unit 272, with the rotation axis direction (third axis $O_3$ direction) being a direction approximately parallel to the extension direction of the part corresponding to the long side of the second arm unit 272. The third axis $O_3$ is a rotation axis approximately perpendicular to the first axis $O_1$ and the second axis $O_2$, and in the example illustrated in FIG. 1, is provided as a rotation axis approximately parallel to the x-axis. By having the microscope unit 110, the first arm unit 271, and the second arm unit 272 rotate about the third axis $O_3$ as a rotation axis by the third rotation axis unit 230, the position in the y-axis direction of the microscope unit 110 is adjusted.

In this way, the support unit 120 is configured so that as a result of rotation about the second axis $O_2$ and the third axis $O_3$ being controlled respectively, the orientation of the microscope unit 110 is controlled. In other words, the second rotation axis unit 220 and the third rotation axis unit 230 may be the rotation axis units that prescribe the orientation of the microscope unit 110.

The leading end of the top side of the parallelogram link mechanism 240 is connected to the base end side of the third rotation axis unit 230. The parallelogram link mechanism 240 is made up of four arms (arms 241, 242, 243, and 244) arranged in a parallelogram shape, and four joint units (joint units 245, 246, 247, and 248) respectively provided at positions corresponding to the approximate vertices of the parallelogram.

The leading end of the arm 241 extending in a direction approximately parallel to the third axis O3 is connected to the third rotation axis unit 230. The joint unit 245 is provided near the leading end of the arm 241, while the joint unit 246 is provided near the base end of the arm 241. The leading end of the arms 242 and 243 are connected to the joint units 245 and 246, respectively, allowing rotation about respective rotation axes (fourth axis $O_4$) approximately perpendicular to the extension direction of the arm 241 and approximately parallel to each other. Furthermore, the joint units 247 and 248 are provided on the base end of the arms 242 and 243, respectively. The leading end and the base end of the arm 244 are connected to these joint units 247 and 248, respectively, allowing rotation about the fourth axis $O_4$, and also approximately parallel to the arm 241.

In this way, the four joint units constituting the parallelogram link mechanism 240 include rotation axes (fourth axis $O_4$) approximately parallel to each other and approximately in the same direction, which operate in conjunction with each other about the fourth axis $O_4$, in the example illustrated in FIG. 1, the fourth axis $O_4$ is provided as a rotation axis approximately parallel to the y-axis. In other words, the parallelogram link mechanism 240 includes multiple joint units that rotate in conjunction with each other around rotation axes disposed in mutually different positions but in the same direction, and fulfills the role of a transmission mechanism that transmits an operation on one end to the other end. By providing the parallelogram link mechanism 240, the motion of the configuration on the leading end side past the parallelogram link mechanism 240 (that is, the microscope unit 110, the first rotation axis unit 210, the second rotation axis unit 220, the third rotation axis unit 230, the first arm unit 271, and the second arm unit 272) is transmitted to the base end side of the parallelogram link mechanism 240.

On a part of the arm 242 separated a certain distance from the base end, there is provided the fifth rotation axis unit 250 that rotatable supports the parallelogram link mechanism 240, with the rotation axis direction (fifth axis $O_5$ direction) being a direction perpendicular to the extension direction of the arm 242. The fifth axis $O_5$ is a rotation axis approximately parallel to the fourth axis $O_4$, and in the example illustrated in FIG. 1, is provided as a rotation axis approximately parallel to the y-axis. The leading end of the third arm unit 273 running in the z-axis direction is connected to the fifth rotation axis unit 250, and the microscope unit 110, the first arm unit 271, the second arm unit 272, and the parallelogram link mechanism 240 are allowed to rotate with respect to the third arm unit 273 via the fifth rotation axis unit 250, with the rotation axis being the fifth axis $O_5$.

The third arm unit 273 is approximately L-shaped, with the base end side curved to be approximately parallel to the floor. The sixth rotation axis unit 260 that allows the third arm unit 273 to rotate about a rotation axis (sixth axis $O_6$) orthogonal to the fifth axis $O_5$ is connected to the face approximately parallel to the floor on the third arm unit 273.

In the example illustrated in FIG. 1, the sixth axis $O_6$ is provided as a rotation axis approximately parallel to the z-axis.

In the illustrated example, the sixth rotation axis unit 260 is integrated with the fourth arm unit 274 that extends in the vertical direction. In other words, the leading end of the fourth arm unit 274 is connected to the face approximately parallel to the floor on the base end of the third arm unit 273. Also, the base end of the fourth arm unit 274 is connected to the top face of the platform 131 of the base unit 130. With this configuration, via the sixth rotation axis unit 260, the microscope unit 110, the first arm unit 271, the second arm unit 272, the parallelogram link mechanism 240, and the third arm unit 273 rotate with respect to the base unit 130, with the rotation axis being the sixth axis $O_6$.

The arm 244 constituting the bottom side of the parallelogram link mechanism 240 is formed to be longer than the arm 241 constituting the top side, and the end of the arm 242 which is positioned diagonally opposite the part where the third rotation axis unit 230 is connected on the parallelogram link mechanism 240 is extended to outside of the parallelogram link mechanism 240. On the extended end of the arm 244, the counterweight 280 is provided. The mass and the placement of the counterweight 280 are adjusted so that the angular moment produced about the fourth axis $O_4$ and the angular moment produced about the fifth axis $O_5$ may be cancelled out by the mass of the configuration disposed farther on the leading end side than the counterweight 280 itself (that is, the microscope unit 110, the first rotation axis unit 210, the second rotation axis unit 220, the third rotation axis unit 230, the first arm unit 271, the second arm unit 272, and the parallelogram link mechanism 240).

In addition, the placement of the fifth rotation axis unit 250 is adjusted so that the center of gravity of the configuration disposed farther on the leading end side than the fifth rotation axis unit 250 is positioned on the fifth axis $O_5$. Furthermore, the placement of the sixth rotation axis unit 260 is adjusted so that the center of gravity of the configuration disposed farther on the leading end side than the sixth rotation axis unit 260 is positioned on the sixth axis $O_6$.

By configuring the mass and placement of the counterweight 280, the placement of the fifth rotation axis unit 250, and the placement of the sixth rotation axis unit 260 in this way, the support unit 120 may be configured as a balance arm that maintains equilibrium of the moment of the microscope unit 110 and the support unit 120 as a whole. By configuring the support unit 120 as a balance arm, when the surgeon attempts to move the microscope unit 110 with a direct operation, the surgeon becomes able to move the microscope unit 110 with less external force, almost like a weightless state. Consequently, user operability may be improved.

Each of the first rotation axis unit 210 to the sixth rotation axis unit 260 of the support unit 120 is provided with a brake that restrains rotation in the first rotation axis unit 210 to the sixth rotation axis unit 260, respectively. Note that for the parallelogram link mechanism 240, since the four joint units (joint units 245 to 248) rotate in conjunction with each other, it is sufficient to provide the brake for the parallelogram link mechanism 240 on at least one of these four joint units. The driving of these brakes is controlled by the control device 140. By releasing these brakes all at once under control from the control device 140, the operating mode of the support unit 120 switches to the free mode. Also, by similarly driving these brakes all at once under control from the control device 140, the operating mode of the support unit 120 switches to the locked mode.

Note that for the brakes provided in the first rotation axis unit 210 to the sixth rotation axis unit 260, any of various types of brakes used in a typical balance arm may be applied, and the specific mechanism is not limited. For example, these brakes may be mechanically driven, or may also be electrically driven electromagnetic brakes.

The above thus describes a configuration of the observation system 1 according to the present embodiment and the observation device 10 according to the present embodiment with reference to FIG. 1. As described above, in the observation device 10 according to the present embodiment, a vibration sensor 113 for detecting vibration of the imaging unit 111 is provided. Also, the control device 140 includes a function of detecting the vibration mode of the imaging unit 111. Additionally, the control device 140 performs image shake correction based on the decided vibration mode and the detection value from the vibration sensor 113. Consequently, it becomes possible to obtain a stable image with less image shake.

Note that in the present embodiment, each of the first rotation axis unit 210 to the sixth rotation axis unit 260 may also be provided with a vibration suppression mechanism. Such a vibration suppression mechanism is a dynamic vibration absorber, for example, is made of a vibration-damping member such as a damper, and is able to suppress vibration in each rotation axis unit.

Figure 2:
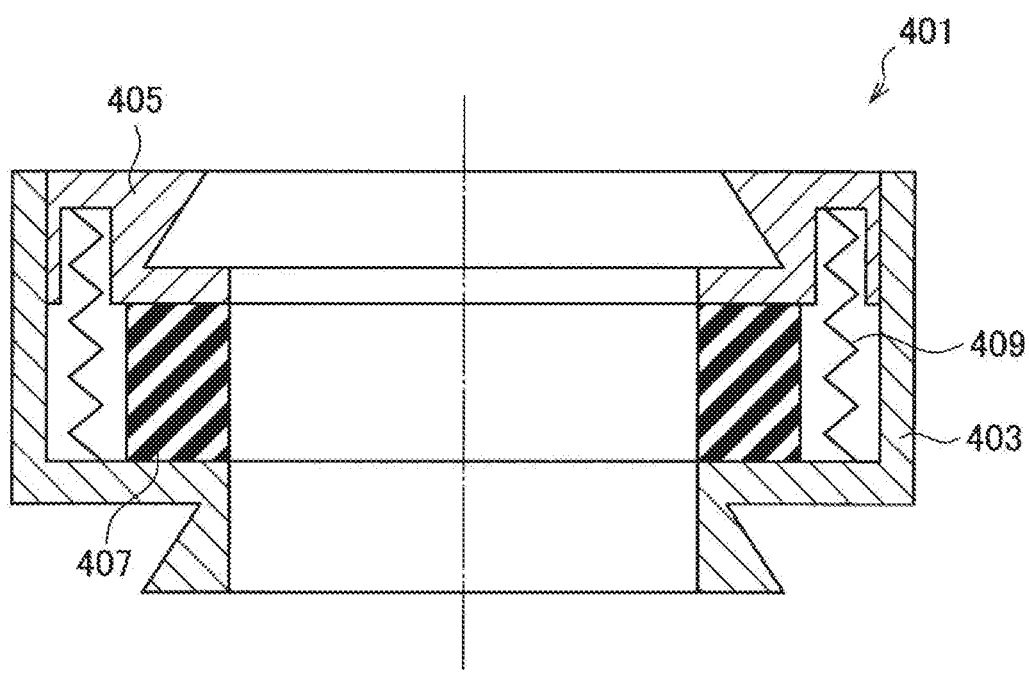
FIG. 2 is a diagram illustrating an example configuration of a vibration suppression mechanism that may be provided in each rotation axis unit.

At this point, several specific example configurations of a vibration suppression mechanism that may be provided in each rotation axis unit of the support unit 120 will be described with reference to FIGS. 2 and 3. FIG. 2 is a diagram illustrating an example configuration of a vibration suppression mechanism that may be provided in each rotation axis unit. Referring to FIG. 2, a vibration suppression mechanism 401 is provided between a barrel-shaped first member 403 and a second member 405 when connecting these two members, and has a function of suppressing the transmission of vibration between these two members. Specifically, in the example configuration, the second member 405 (weighted member 405) is fitted inside the barrel-shaped first member 403 to be damped (damped member 403) so as to allow the second member 405 to slide in the axial direction (the up-and-down direction in the drawing), thereby connecting the two members together. At this point, a viscoelastic member 407 acting as a viscous drag element and a spring 409 are provided between the damped member 403 and the weighted member 405. The vibration suppression mechanism 401 is a dynamic vibration absorber made up of the viscoelastic member 407 and the spring 409. Note that the viscoelastic member 407 has both mechanical properties and spring-like properties, and is made of a rubber material such as silicon rubber or urethane rubber, for example.

The viscoelastic member 407 and the spring 409 expands and contracts in the axial direction in response to vibration of the damped member 403 and the weighted member 405, and has a function of attenuating the vibration. The natural frequency of the vibration suppression mechanism 401 is decided according to the characteristics of the viscoelastic member 407 and the spring 409, but the damping effect is maximally exhibited when this natural frequency approximately matches the natural frequency of the support unit 120 to be damped. Consequently, the vibration suppression mechanism 401 may be configured to allow the viscoelastic member 407 and the spring 409 to be interchanged with parts having different characteristics. Consequently, the vibration suppression mechanism 401 may be configured appropriately according to the configuration of the support unit 120 so that the natural frequency of the vibration suppression mechanism 401 approximately matches the natural frequency of the support unit 120, and a large damping effect may be obtained.

Figure 3:
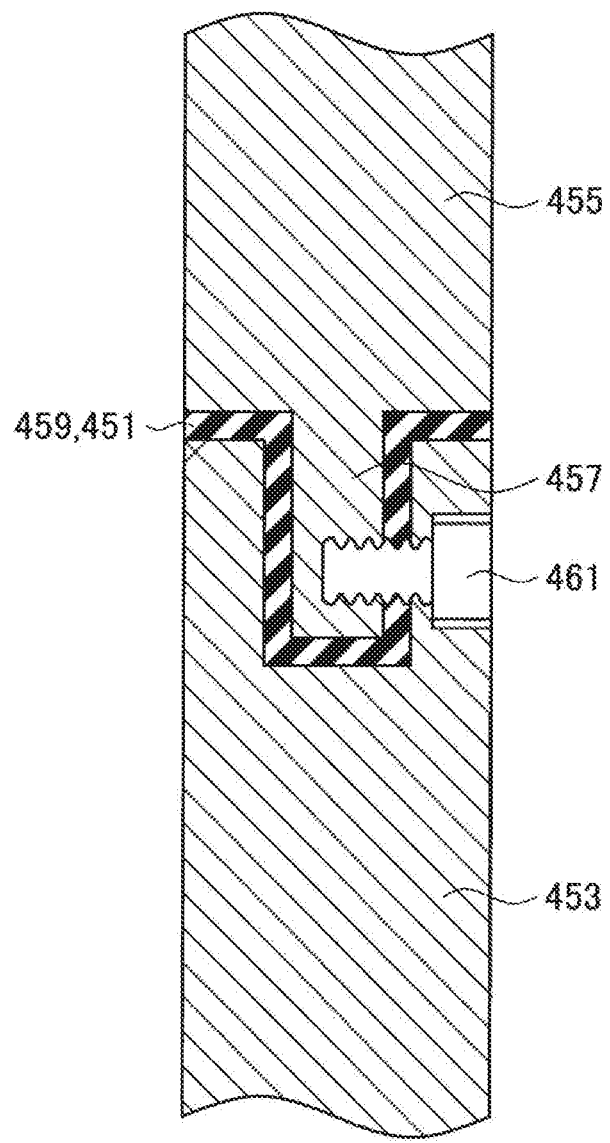
FIG. 3 is a diagram illustrating another example configuration of a vibration suppression mechanism that may be provided in each rotation axis unit.

In addition, FIG. 3 is a diagram illustrating another example configuration of a vibration suppression mechanism that may be provided in each rotation axis unit. Referring to FIG. 3, a vibration suppression mechanism 451 is provided between an approximately rod-shaped first member 453 and a second member 455 when connecting these two members, and has a function of suppressing the transmission of vibration between these two members. Specifically, in this example configuration, a concave seat 459 formed from an elastic material capable of absorbing vibration, such as rubber, is provided on the connecting end of the first member 453. Also, an axial unit 457 formed with a narrower diameter than other parts is provided on the connecting end of the second member 455. Subsequently, with the axial unit 457 of the second member 455 inserted into the concavity of the seat 459, the first member 453, the seat 459, and the axial unit 457 are secured by a screw 461, thereby connecting the first member 453 and the second member 455 together. The seat 459 may constitute the vibration suppression mechanism 451 that absorbs slight vibration. Note that at this point, an elastic material (not illustrated) capable of absorbing vibration, such as rubber, may also be interposed between the screw 461 and the first member 453, and the vibration suppression mechanism 451 may be made up of the seat 459 and the elastic member.

As illustrated, since the seat 459 has a concave shape, vibration in all three axis directions may be suppressed favorably. In this way, according to the vibration suppression mechanism 451, the transmission of vibration produced in either one of the first member 453 and the second member 455 to the other may be suppressed more effectively.

The above thus describes several example configurations of a vibration suppression mechanism that may be provided in each rotation axis unit of the support unit 120 with reference to FIGS. 2 and 3. Note that any of various known types of mechanisms other than those illustrated herein may also be used as such a vibration suppression mechanism.

By providing such a vibration suppression mechanism, vibration of the microscope unit 110 (that is, the imaging unit 111) is suppressed, and thus an image with even less image shake may be obtained. In other words, in the present embodiment, for the correction (suppression) of image shake, what may be termed active image shake correction may be performed by the control device 140 as discussed earlier, and in addition, what may be termed passive image shake suppression may also be performed by the vibration suppression mechanism provided in the first rotation axis unit 210 to the sixth rotation axis unit 260. In this way, by combining two types of methods, namely a software-based method and a hardware-based method, it becomes possible to perform image shake correction more effectively.

2. Details of Image Shake Correction Process

Figure 4:
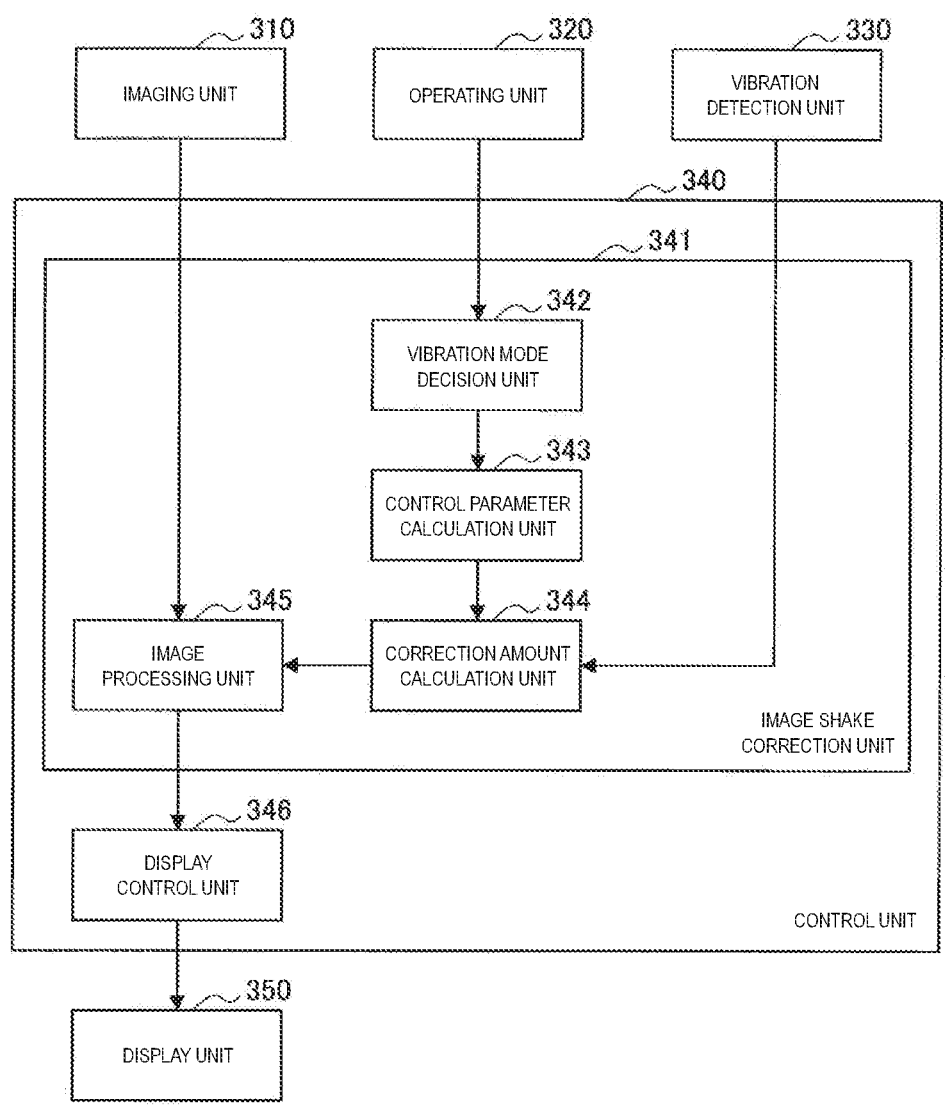
FIG. 4 is a block diagram illustrating an example of a functional configuration of a control unit that realizes an image shake correction process according to an embodiment.

An image shake correction process according to the present embodiment, executed in the observation device 10 described above, will now be described in detail with reference to FIG. 4. FIG. 4 is a block diagram illustrating an example of a functional configuration of a control unit for realizing an image shake correction process according to the present embodiment.

Referring to FIG. 4, a control unit 340 for realizing an image shake correction process according to the present embodiment functionally includes an image shake correction unit 341 and a display control unit 346. Additionally, the image shake correction unit 341 functionally includes a vibration mode decision unit 342, a control parameter calculation unit 343, a correction amount calculation unit 344, and an image processing unit 345. By including these functions of the control unit 340 onboard the control device 140 illustrated in FIG. 1, an image shake correction process is executed in the observation device 10.

In FIG. 4, for the sake of explanation, other function blocks besides the control unit 340 are also illustrated. The imaging unit 310 corresponds to the imaging unit 111 of the microscope unit 110 illustrated in FIG. 1. The imaging unit 310 provides information about a captured image of the surgical site to the image processing unit 345.

The operating unit 320 corresponds to an input device by which the surgeon issues instruction input to the observation device 10, such as the various switches (zoom SW 151, focus SW 152, and operating mode toggle SW 153) provided on the microscope unit 110 illustrated in FIG. 1. Information about the surgeon's operating input with respect to the operating unit 320 is provided to the vibration mode decision unit 342.

The vibration detection unit 330 corresponds to the vibration sensor 113 provided in the microscope unit 110 illustrated in FIG. 1. The vibration detection unit 330 provides a detection value of vibration of the imaging unit 111 to the correction amount calculation unit 344.

The display unit 350 corresponds to the display device 20 illustrated in FIG. 1. The display unit 350, under control from the display control unit 346, displays a surgical site image that has been subjected to image shake correction.

The functions of the control unit 340 will be described in detail. The vibration mode decision unit 342 decides the vibration mode of the imaging unit 111, based on information about the surgeon's operating input with respect to the operating unit 320. Herein, the vibration mode refers to a classification of the state of vibration of the imaging unit 111 according to the characteristics of the vibration.

In the present embodiment, the following three vibrations are anticipated as vibrations that may occur in the imaging unit 111 during surgery.

Vibration 1: Footstep Vibration

Vibration produced by persons such as medical staff walking inside the operating room. The frequency of such vibration is approximately from 1 Hz to 100 Hz, for example.

Vibration 2: Imaging Unit Movement Vibration

Vibration produced as a result of the surgeon moving the microscope unit 110 (that is, the imaging unit 111) in the free mode. The frequency of such vibration is approximately from 1 Hz to 15 Hz, for example.

Vibration 3: Imaging Unit Locking Vibration

Vibration produced after moving and positioning the microscope unit 110 (that is, the imaging unit 111), as a result of the surgeon switching from the free mode to the locked mode, and releasing his or her hand from the microscope unit 110. The frequency of such vibration is approximately from 0.1 Hz to 10 Hz, for example.

The vibration mode decision unit 342 judges which of these vibrations has a high likelihood of occurring in the imaging unit 111, and decides the vibration mode of the imaging unit 111 as one of these vibrations, or as a combination of these vibrations.

Specifically, footstep vibration has a high likelihood of occurring continuously during surgery. Consequently, the vibration mode decision unit 342 judges that footstep vibration has a high likelihood of occurring in the imaging unit 111, irrespectively of the surgeon's operating input with respect to the operating unit 320.

On the other hand, imaging unit movement vibration and imaging unit locking vibration is produced according to operations on the microscope unit 110 by the surgeon, as described above. At this point, while the surgeon is pressing the operating mode toggle SW 153, the operating mode of the support unit 120 is the free mode, and thus there is a high likelihood of imaging unit movement vibration occurring. Also, the instant at which the surgeon releases his or her hand from the operating mode toggle SW 153 is the instant at which the operating mode of the support unit 120 switches from the free mode to the locked mode, and thus there is a high likelihood of imaging unit locking vibration occurring for a certain time after that.

Consequently, while the operating mode toggle SW 153 is being pressed (in other words, while information indicating that the operating mode toggle SW 153 is being pressed is being input from the operating unit 320 as information about the surgeon's operating input), the vibration mode decision unit 342 judges that there is a high likelihood that imaging unit movement vibration is occurring in the imaging unit 111. Also, for a certain time after the operating mode toggle SW 153 changes from a pressed state to a released state (in other words, for a certain time after information indicating that the operating mode toggle SW 153 changed from the pressed state to the released state is input from the operating unit 320 as information about the surgeon's operating input), the vibration mode decision unit 342 judges that there is a high likelihood that imaging unit locking vibration is occurring in the imaging unit 111.

To summarize, in the present embodiment, the vibration mode decision unit 342 decides the following three types of vibration modes, according to the surgeon's operating input with respect to the operating unit 320.

While the operating mode toggle SW 153 is being pressed, the vibration mode decision unit 342 decides an operating mode in which both footstep vibration and imaging unit movement vibration are occurring in the imaging unit 111 (hereinafter also designated vibration mode 1).

In addition, when the operating mode toggle SW 153 changes from a pressed state to a released state, for a certain time afterward, the vibration mode decision unit 342 decides an operating mode in which both footstep vibration and imaging unit locking vibration are occurring in the imaging unit 111 (hereinafter also designated vibration mode 2). Note that the certain time may be decided based on experiment, simulation, or the like. For example, the vibration occurring in the microscope unit 110 (imaging unit 111) after locking the position of the microscope unit 110 and releasing one's hand may be measured actually, or calculated by simulation, and by conducting frequency analysis or the like on the measurement result or the calculation result and investigating the time over which vibration thought to be imaging unit locking vibration continues, the certain time may be decided.

In addition, in cases other than the above, the vibration mode decision unit 342 decides an operating mode in which footstep vibration is occurring in the imaging unit 111 (hereinafter also designated vibration mode 3).

The vibration mode decision unit 342 provides information about the decided vibration mode of the imaging unit 111 to the control parameter calculation unit 343. Note that information about the vibration mode (for example, information about the type of vibration mode and information about the types of vibration included in each vibration mode) may also be stored in advance in a storage unit (not illustrated) provided in the observation device 10. For example, as the information about the vibration mode, information about vibration predicted to occur possibly in the imaging unit 111 and information about vibration modes of the imaging unit 111 which may be predicted may be input into the storage unit in advance by a person such as the surgeon or a designer of the observation system 1. By referencing the storage unit, the vibration mode decision unit 342 may select and decide an appropriate vibration mode according to the surgeon's operations from among several preset vibration modes.

The control parameter calculation unit 343 calculates a control parameter for image shake correction, based on the vibration mode of the imaging unit 111 decided by the vibration mode decision unit 342.

Herein, in the present embodiment, either of an electronic correction method and an optical correction method may be used as the method of image shake correction. An electronic correction method is a method of correcting image shake by correcting the observation light capture position for each pixel of the image sensor, based on the detected vibration state, at the stage of image processing on the image signal acquired by the image sensor. On the other hand, an optical correction method is a method of correcting image shake by moving the optical system of the imaging unit 310 (such as a lens, for example) or the position of the image sensor, based on the detected vibration state, and thereby adjusting the light-sensing position for observation light in the image sensor.

However, when these methods are compared, the optical correction method involves a driving mechanism that moves the lens or image sensor. In contrast, the electronic correction method is executable by electronic processing on the image signal, and thus the configuration of the microscope unit 110 may be made simpler and more compact. For this reason, in the present embodiment, the electronic correction method preferably is used. Note that the functional configuration of the control unit 340 illustrated in FIG. 4 also illustrates a functional configuration corresponding to a case in which the electronic correction method is used in the image shake correction process. Additionally, the description of the control unit 340 hereinafter also takes a case in which the electronic correction method is used as an example.

The control parameter calculation unit 343, based on the vibration mode of the imaging unit 111, is able to obtain information about the state of the presumed vibration occurring in the imaging unit 111 (such as the frequency characteristics, for example). For example, if the vibration mode 1 has been decided, the control parameter calculation unit 343 is able to judge that combined vibration from footstep vibration (for example, vibration with a frequency approximately from 1 Hz to 100 Hz) and imaging unit movement vibration (for example, vibration with a frequency approximately from 1 Hz to 15 Hz) is occurring in the imaging unit 111. The control parameter calculation unit 343 analyzes the vibration by using the fast Fourier transform (FFT) or the like, and acquires characteristics of the vibration (such as gain characteristics and phase characteristics, for example).

Additionally, the control parameter calculation unit 343, based on the characteristics of the vibration corresponding to the vibration mode, calculates various control parameters used to calculate a correction amount in the electronic correction method (specifically, the capture positions of pixels in the image sensor, the change over time in the capture positions, and the like). The control parameters may be similar to parameters used in any of various known electronic correction methods. For example, the control parameter calculation unit 343 calculates the filter characteristics of various filters (high-pass filter (HPF) and low-pass filter (LPF)), an integration coefficient, and a phase compensation amount as the control parameters.

The control parameter calculation unit 343 provides information about the calculated control parameters to the correction amount calculation unit 344. Note that the control parameter calculation unit 343 is able to execute a process of calculating the control parameters described above by referencing the storage unit in which the information about the vibration mode discussed above is stored.

The correction amount calculation unit 344 calculates a correction amount for performing image shake correction, based on the control parameters calculated by the control parameter calculation unit 343 and the detection value of vibration of the imaging unit 111 provided by the vibration detection unit 330. In the case of the example configuration illustrated in FIG. 4, the correction amount calculation unit 344 calculates the capture positions of pixels in the image sensor, the change over time in the capture positions, and the like as correction amounts related to electronic image shake correction. The correction amount calculation unit 344 provides information about the calculated correction amount to the image processing unit 345.

The image processing unit 345 performs various types of image processing on the image signal acquired by the imaging unit 310 to cause the display unit 350 to display an image based on the image signal. For the image processing, various types of signal processing typically conducted for image display may be conducted, such as gamma correction, white balance adjustment, magnification and pixel interpolation related to an electronic zoom function, and the like, for example. In these processes, any of various known techniques may be used, and thus detailed description is omitted herein.

Additionally, in the image processing, the image processing unit 345 executes image shake correction based on the correction amount calculated by the correction amount calculation unit 344. For example, the image processing unit 345 corrects image shake by generating an image in which the capture position of the observation image is shifted according to the correction amount.

Note that in the control parameter calculation process by the control parameter calculation unit 343, the correction amount calculation process by the correction amount calculation unit 344, and the image processing related to image shake correction by the image processing unit 345, any of various known methods typically used as an electronic correction method in the technical field of shake correction in an imaging device such as a digital camera, for example, may be used, and thus detailed description is omitted herein.

The image processing unit 345 provides the display control unit 346 with an image signal that has been subjected to various types of image processing, including image shake correction. The display control unit 346 drives the display unit 350, and causes the display unit 350 to display an image of the surgical site based on the image signal subjected to such image processing. Consequently, a stable image less affected by vibration, and in which image shake has been corrected, is displayed on the display unit 350, and the visibility of the surgical site to the surgeon is improved. Consequently, safer and smoother execution of surgery may be realized.

At this point, according to the present embodiment, the vibration mode of the imaging unit 111 is decided from the current state of the support unit 120, and an image shake correction process that also accounts for the vibration mode is conducted. Consequently, an optimal image shake correction process according to the vibration mode of the imaging unit 111 may be conducted, making it possible to conduct image shake correction more precisely. Additionally, in a case in which an image shake correction function according to the present embodiment is installed onboard an existing observation device, if the electronic correction method is adopted, in terms of hardware, it is sufficient merely to add the vibration sensor 113 to the microscope unit 110. Consequently, it becomes possible to realize the observation device 10 with an image shake correction function according to the present embodiment installed onboard at comparatively low cost.

Many typical digital cameras and the like have a handheld shake correction function installed onboard. However, the handheld shake correction function installed onboard such digital cameras and the like corrects image shake caused by vibration produced as a result of the user holding the digital camera in his or her hands. Consequently, if the handheld shake correction function is activated for shooting when the camera is not being held in hand, such as when the camera is affixed to a tripod, for example, there is a possibility of actually worsening image quality instead. In this way, the handheld shake correction function onboard imaging devices such as digital cameras of the related art, it is difficult to conduct appropriate image shake correction corresponding to the shooting conditions. In contrast, according to the present embodiment, since image shake correction that also accounts for the vibration mode of the imaging unit 111, or in other words the conditions of vibration of the imaging unit 111, as discussed earlier, it becomes possible to conduct more appropriate image shake correction.

The above thus describes a functional configuration of the control unit 340 that executes an image shake correction process according to the present embodiment with reference to FIG. 4.

Figure 5:
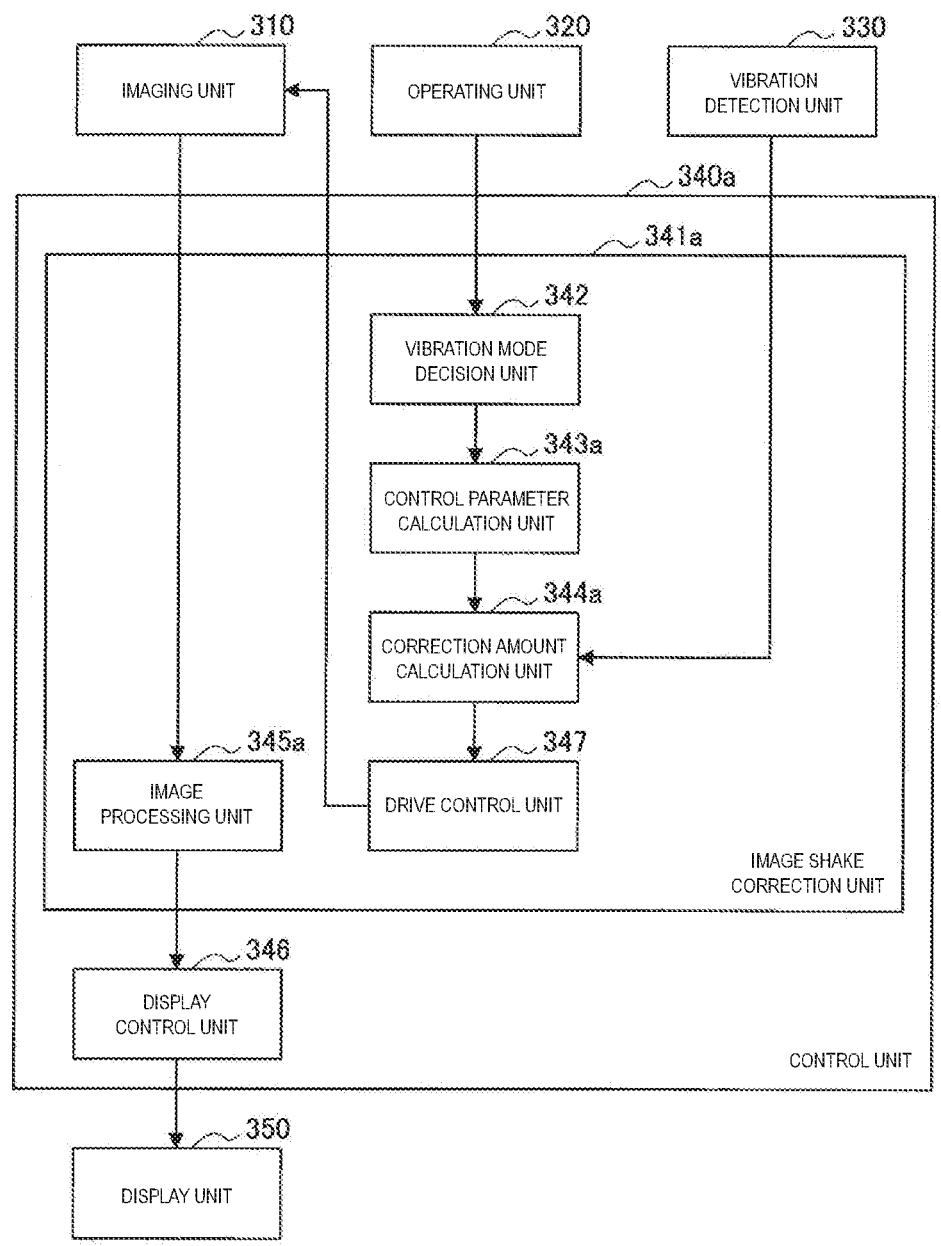
FIG. 5 is a block diagram illustrating an example of a functional configuration of a control unit that realizes an image shake correction process according to a modification of an embodiment.

Herein, as discussed earlier, in the image shake correction process according to the present embodiment, an optical correction method rather than an electronic correction method may also be used. As a modification of the present embodiment, a configuration of the control unit in the case in which the optical correction method is used will be described. FIG. 5 is a block diagram illustrating an example of a functional configuration of a control unit that realizes an image shake correction process according to a modification of the present embodiment.

Referring to FIG. 5, the control unit 340a according to the present modification functionally includes an image shake correction unit 341a and a display control unit 346. Additionally, the image shake correction unit 341a functionally includes a vibration mode decision unit 342, a control parameter calculation unit 343a, a correction amount calculation unit 344a, an image processing unit 345a, and a drive control unit 347.

Note that the function configuration of the control unit 340a corresponds to changing the method of image shake correction to the optical correction method in the control unit 340 described earlier. Specifically, the functional configuration of the control unit 340a corresponds to partially changing the functions of the control parameter calculation unit 343, the correction amount calculation unit 344, and the image processing unit 345 in the control unit 340 illustrated in FIG. 4, and also adding the drive control unit 347. Since the details of the other functions are mostly similar to the functions corresponding to the control unit 340, description will be reduced or omitted herein.

In the present modification, the control parameter calculation unit 343a calculates a parameter corresponding to the optical correction method as a control parameter for image shake correction. Known optical correction methods include a technique of moving the optical system that guides observation light to the image sensor in the imaging unit 310 based on the vibration state (lens shift technique), and a technique of moving the image sensor in the imaging unit 310 based on the vibration state (imager shift technique), for example.

The control parameter calculation unit 343a, similarly to the control parameter calculation unit 343 discussed earlier, analyzes the vibration corresponding to the vibration mode by using the fast Fourier transform or the like, and acquires characteristics of the vibration (such as gain characteristics and phase characteristics, for example). Additionally, the control parameter calculation unit 343a follows the adopted correction technique, and based on the characteristics of the analyzed vibration, calculates various control parameters used to calculate a correction amount in the optical correction method (specifically, a displacement amount of the optical system and the displacement change over time, or a displacement amount of the image sensor amount and the displacement change over time, or the like).

The control parameters may be similar to parameters calculated in any of various known optical correction methods. For example, the control parameter calculation unit 343a calculates the filter characteristics of various filters (HPF and LPF), an integration coefficient, and a phase compensation amount as the control parameters. The control parameter calculation unit 343a provides information about the calculated control parameters to the correction amount calculation unit 344a.

The correction amount calculation unit 344a calculates a correction amount for performing image shake correction, based on the control parameters calculated by the control parameter calculation unit 343a and the detection value of vibration of the imaging unit 111 provided by the vibration detection unit 330. In the case of the example configuration illustrated in FIG. 5, the correction amount calculation unit 344a follows the adopted correction technique and calculates a displacement amount of the optical system and displacement change over time, or a displacement amount of the image sensor and displacement change over time, or the like as correction amounts related to optical image shake correction. The correction amount calculation unit 344a provides information about the calculated correction amount to the drive control unit 347.

In the present modification, the imaging unit 310 includes a drive mechanism, such as an actuator for moving the position of the optical system or the image sensor, according to the adopted image shake correction technique. The drive control unit 347 controls the driving of such a drive mechanism, and moves the optical system or the image sensor in accordance with the correction amount calculated by the correction amount calculation unit 344a. In the present modification, as a result, there is obtained an image signal that has been subjected to image shake correction during the shooting of the surgical site. In other words, the imaging unit 310 provides the image processing unit 345a with an image signal that has been subjected to image shake correction.

The image processing unit 345a, similarly to the image processing unit 345 discussed earlier, performs various types of image processing on the image signal acquired by the imaging unit 310 to cause the display unit 350 to display an image based on the image signal. At this point, the present modification differs from the embodiment discussed earlier in that the image processing unit 345a does not conduct image processing related to image shake correction, but instead conducts only various types of image processing for general image display. This is because, as described above, in the present modification, there is obtained an image signal that has been subjected to image shake correction during the shooting of the surgical site.

Note that in the control parameter calculation process by the control parameter calculation unit 343a and the correction amount calculation process by the correction amount calculation unit 344a, any of various known methods typically used as an electronic correction method in the technical field of shake correction in an imaging device such as a digital camera, for example, may be used, and thus detailed description is omitted herein.

The following process is similar to the embodiment discussed earlier. In other words, the image processing unit 345a provides the display control unit 346 with an image signal that has been subjected to image processing, and the display control unit 346 drives the display unit 350 and causes the display unit 350 to display an image of the surgical site based on the image signal subjected to such image processing.

The above thus describes a functional configuration of the control unit 340a according to a modification of the present embodiment. Even with the configuration according to the present modification, it becomes possible to obtain a more stable image less affected by vibration, similarly to the foregoing embodiment. As discussed above, although typically the electronic correction method is considered to have an advantage in being realizable at low cost compared to the optical correction method, but depending on factors such as the configuration of the observation device 10 to which image shake correction according to the present embodiment is to be applied, the optical correction method may be considered easier to adopt in some cases, such as if the optical correction method is simple to implement, for example. Alternatively, even with the optical correction method, in the case of the lens shift technique, it is sufficient to provide a moving coil and a movable lens as the drive mechanism of the optical system, for example, and thus is realizable at comparatively low cost compared to the imager shift technique. Whether to adopt the configuration according to the foregoing embodiment or the configuration according to the present modification may be selected appropriately in consideration of factors such as cost and the ease of implementation.

Note that the foregoing description supposes three vibration types for the vibration of the imaging unit 111, as well as three vibration modes (vibration modes 1 to 3) based on these vibration types. However, these three vibration types and three vibration modes are merely one example, and in the present embodiment, various other types of vibrations which may occur in the imaging unit 111 may also be considered, and a vibration mode may be decided appropriately according to such other types of vibrations. For example, if a device that may produce vibration, such as a compressor, exists inside the operating room, vibration produced in the imaging unit 111 due to the vibration of the compressor may also be considered when deciding the vibration mode. Alternatively, if one of the rotation axis units of the support unit 120 of the observation device 10 is provided with an actuator for driving that rotation axis unit, the vibration produced in the imaging unit 111 due to the vibration of a motor in the actuator may also be considered when deciding the vibration mode.

Also, in the above description, for example, the frequency of footstep vibration is prescribed to be approximately from 1 Hz to 100 Hz, while the frequency of imaging unit movement vibration is prescribed to be approximately from 1 Hz to 15 Hz, and the frequency of imaging unit locking vibration is prescribed to be approximately from 0.1 Hz to 10 Hz. However, these frequency bands are merely one example. The anticipated characteristics of each vibration may vary depending on the configuration of the support unit 120 and the type of the vibration source, for example. Consequently, it is preferable if the characteristics of each vibration constituting a vibration mode are prescribed respectively to match reality, such as by experiment or simulation, for example.

Also, in the control parameter calculation process by the control parameter calculation unit 343 or 343a, and/or the correction amount calculation process by the correction amount calculation unit 344 or 344a, the magnification and/or the focal length of the microscope unit 110 may also be considered. This is because the observation image to correct also changes depending on the magnification and the focal length of the microscope unit 110. In this case, information about the surgeon's operations with respect to the zoom SW 151 and/or the focus SW 152 may also be provided from the operating unit 320 to the control parameter calculation unit 343 or 343a and/or the correction amount calculation unit 344 or 344a. Based on such information, the control parameter calculation unit 343 or 343a and/or the correction amount calculation unit 344 or 344a ascertain the magnification and/or the focal length of the microscope unit 110 when an image signal is acquired, and are able to take this information into account to calculate a control parameter and/or a correction amount, respectively.

Herein, the respective functions of the control units 340 and 340a discussed earlier are realized by having a processor such as a CPU operate according to a certain computer program. It is also possible to develop a computer program for realizing the respective functions of the control units 340 and 340a, and implement the computer program in a personal computer or the like. In addition, a computer-readable recording medium storing such a computer program may also be provided. The recording medium may be a magnetic disc, an optical disc, a magneto-optical disc, or flash memory, for example. Furthermore, the above computer program may also be delivered via a network, for example, without using a recording medium.

3. Image Shake Correction Method

Figure 6:
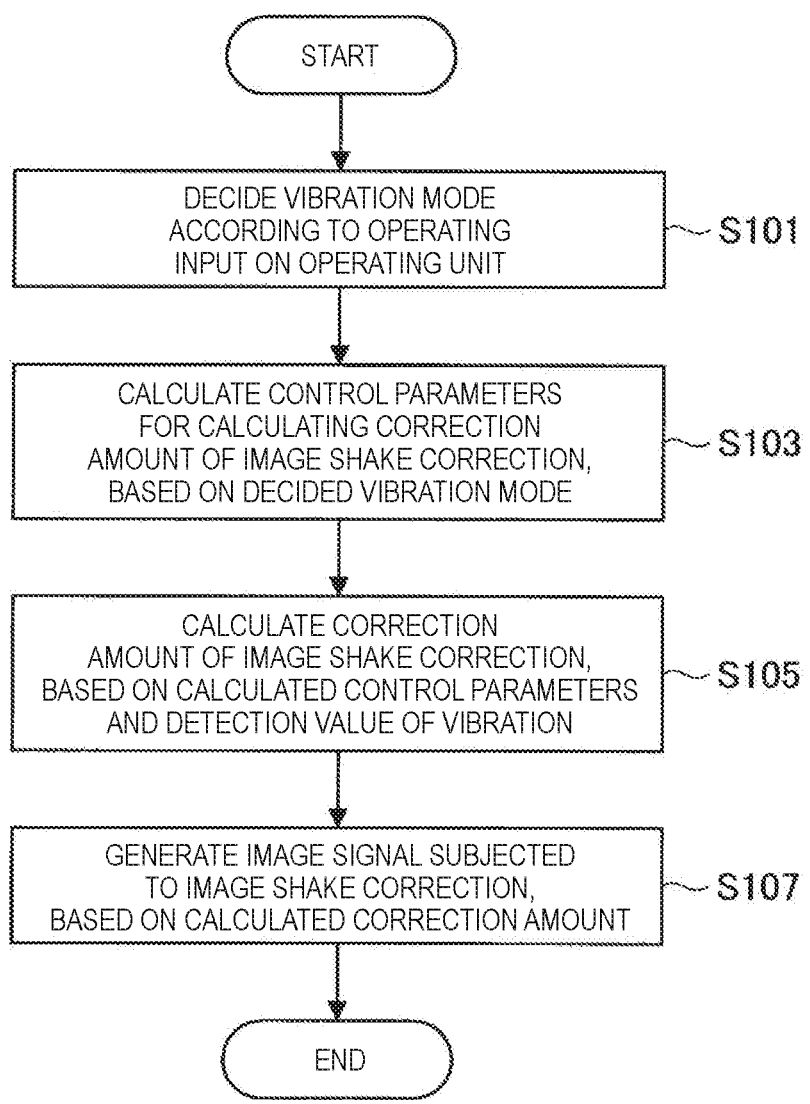
FIG. 6 is a flowchart illustrating an example of a processing procedure of an image shake correction method according to an embodiment.

A processing procedure of an image shake correction method according to the present embodiment will now be described with reference to FIG. 6. FIG. 6 is a flowchart illustrating an example of a processing procedure of an image shake correction method according to the present embodiment. Note that each process illustrated in FIG. 6 corresponds to a process conducted by the control unit 340 illustrated in FIG. 4 or the control unit 340a illustrated in FIG. 5. Since the content of these processes has been described already with reference to FIG. 4 or 5, detailed description is omitted herein.

Referring to FIG. 6, in the image shake correction method according to the present embodiment, first, a vibration mode is decided according to the surgeon's operating input with respect to the operating unit (step S101). The process illustrated in step S101 corresponds to the process conducted in the vibration mode decision unit 342 illustrated in FIG. 4 or 5.

Next, control parameters for calculating a correction amount of image shake correction are calculated, based on the decided vibration mode (step S103). The process illustrated in step S103 corresponds to the process conducted in the control parameter calculation unit 343 illustrated in FIG. 4 or the control parameter calculation unit 343a illustrated in FIG. 5.

Next, the correction amount of image shake correction is calculated, based on the calculated control parameters and the detection value of vibration (step S105). The process illustrated in step S105 corresponds to the process conducted in the correction amount calculation unit 344 illustrated in FIG. 4 or the correction amount calculation unit 344a illustrated in FIG. 5.

Next, an image signal that has been subjected to image shake correction is generated, based on the calculated correction amount (step S107). Specifically, in the case of conducting image shake correction according to the electronic correction method, in step S107, various types of image processing for image display as well as image processing for image shake correction based on the correction amount are conducted on the image signal acquired by the imaging unit 310 illustrated in FIG. 4, and an image signal in which image shake has been corrected is generated. Alternatively, in the case of conducting image shake correction according to the optical correction method, in step S107, various types of image processing for image display are conducted on the image signal acquired by the imaging unit 310 in a state in which the optical system or the image sensor has been shifted in accordance with the correction amount, and an image signal in which image shake has been corrected is generated. Note that the process illustrated in step S107 corresponds to the process conducted in the image processing unit 345 illustrated in FIG. 4 or the image processing unit 345a illustrated in FIG. 5.

The above thus describes a processing procedure of an image shake correction method according to the present embodiment. By displaying, on a display device, an image based on the image signal obtained in step S107, a stable image less affected by vibration, and in which image shake has been suppressed, may be obtained. Consequently, safer and smoother execution of surgery is realized.

4. Supplemental Remarks

It should be understood by those skilled in the art that various modifications, combinations, sub-combinations and alterations may occur depending on design requirements and other factors insofar as they are within the scope of the appended claims or the equivalents thereof.

Further, the effects described in this specification are merely illustrative or exemplified effects, and are not limitative. That is, with or in the place of the above effects, the technology according to the present disclosure may achieve other effects that are clear to those skilled in the art based on the description of this specification.

For example, in the foregoing embodiment, when conducting the image shake correction process, the correction amount is calculated using both the vibration mode of the imaging unit 111 and the detection value of vibration of the imaging unit 111. However, the present technology is not limited to such an example. For example, the vibration mode decision process may also not be conducted, and the correction amount may be calculated based on only the detection value of vibration of the imaging unit 111. In this case, in the function configuration illustrated in FIGS. 4 and 5, the functions of the vibration mode decision unit 342 and the control parameter calculation unit 343 or 343a are not provided, and the correction amount calculation unit 344 or 344a is able to use typical control parameters, for example, to calculate the correction amount based on only the detection value of vibration of the imaging unit 111 provided by the vibration detection unit 330. Even with such a configuration, the advantageous effects of image shake correction may be obtained to some degree.

However, in the case of conducting image shake correction based on only the detection value of vibration, broadly speaking, correction is conducted to cancel out the detected vibration. In other words, feedback-like control based on the detection value is conducted, and thus depending on the characteristics of the vibration, precise image shake correction may not necessarily be conducted. Additionally, the detection value of vibration may be considered to represent the aggregate of what may be called multiple vibration modes. Consequently, in the case of conducting image shake correction based on only the detection value of vibration, the multiple vibration modes are grasped in aggregate, and image shake correction is conducted to reduce the vibration overall, but since the frequency band of the vibration to reduce is a wide band, there is still a possibility of being unable to conduct precise image shake correction, depending on the characteristics of the vibration.

Accordingly, to conduct more precise image shake correction, it is considered preferable to calculate the correction amount by adjusting the control parameters according to the vibration mode, like in the foregoing embodiment. In this way, by combining the actual detection value of vibration with a vibration mode reflecting the state of the support unit 120, the foregoing embodiment realizes precise image shake correction.

Additionally, in the embodiment described above, the observation device 10 is a microscope device equipped with a microscope unit 110 of the electronic imaging type, but the present technology is not limited to such an example. For example, the observation device 10 may also be a microscope device equipped with a microscope unit of the optical type instead of the microscope unit 110. Note that in this case, since the microscope unit of the optical type is not provided with an imaging unit, it is sufficient to conduct image shake correction similar to that of the imaging unit 111 in the foregoing embodiment, but targeting the microscope unit of the optical type itself. Specifically, for example, in the case of targeting a microscope unit of the optical type, it is sufficient to conduct image shake correction in which the imaging unit movement vibration and the imaging unit locking vibration in the foregoing embodiment are substituted with microscope unit movement vibration and microscope unit locking vibration, respectively. Alternatively, the observation device 10 may also be an endoscopic device equipped with an endoscope (a lens barrel, and a camera head connected to the base end of the lens barrel) instead of the microscope unit 110, for example. Note that in this case, the camera head is supported by the support unit 120, and a configuration similar to the imaging unit 111 discussed earlier is provided inside the camera head. It is sufficient to conduct image shake correction similar to that of the imaging unit 111 in the foregoing embodiment, but targeting the imaging unit inside the camera head. In this way, the present technology is applicable to various types of observation devices, insofar as the observation device uses an arm unit to support an observation unit for performing magnified observation of a surgical site on a patient, and the type of the observation unit is not limited. Since shaking of the observation unit during magnified observation leads to large swings in the field of view, applying the present technology irrespectively of the type of observation unit makes it possible to further suppress shaking of the observation image and execute smooth surgery.

However, in the case of an observation device equipped with a microscope unit of the optical type, only the lens shift technique of the optical correction method is available for adoption as the image shake correction method. Conversely, by applying the present technology to an observation device 10 equipped a microscope unit 110 of the electronic imaging type like in the foregoing embodiment, use of the electronic correction method becomes possible, thereby making it possible to realize the present technology at lower cost.

Additionally, the present technology may also be configured as below.

(1) A medical observation device, including:
an observation unit configured to perform magnified observation of a surgical site;
a vibration sensor that detects a vibration of the observation unit;
a support unit that supports the observation unit; and
a control unit that conducts an image shake correction that corrects a shake in an image observed by the observation unit, based on a detection value from the vibration sensor.

(2) The medical observation device according to (1), wherein
the control unit decides a vibration mode of the observation unit according to a state of the support unit, and conducts the image shake correction based additionally on the decided vibration mode.

(3) The medical observation device according to (2), further including:
an operating unit configured to change an operating mode of the support unit, wherein
the vibration mode is decided according to a user operation on the operating unit.

(4) The medical observation device according to (2) or (3), wherein
the vibration mode is decided as a mode of vibration including a vibration characteristic of at least one from among a footstep vibration produced by a person walking inside an operating room, an observation unit movement vibration produced by the observation unit moving, and an observation unit locking vibration produced by the observation unit being locked at a position after moving.

(5) The medical observation device according to any one of (1) to (4), wherein
the observation unit includes an imaging unit that generates an image by sensing observation light with an image sensor, and
the image shake correction is conducted in accordance with an electronic correction method that corrects a shake in an image by correcting a capture position of observation light for each pixel in the image sensor.

(6) The medical observation device according to any one of (1) to (4), wherein
the image shake correction is conducted in accordance with an optical correction method with a lens shift technique that corrects a shake in an image by moving a position of an optical system that guides observation light in the observation unit.

(7) The medical observation device according to any one of (1) to (4), wherein the observation unit includes an imaging unit that generates an image by sensing observation light with an image sensor, and
the image shake correction is conducted in accordance with an optical correction method with an imager shift technique that corrects a shake in an image by moving a position of the image sensor.

(8) The medical observation device according to any one of (1) to (7), wherein
on a housing of the observation unit, a grip unit gripped by a user when moving the observation unit is provided.

(9) The medical observation device according to any one of (1) to (8), wherein
the support unit includes rotation axis units, and
each of the rotation axis units is provided with a vibration suppression mechanism that suppresses vibration in the rotation axis unit.

(10) The medical observation device according to any one of (1) to (7) or (9), wherein
the observation unit includes an endoscope, and a camera head connected to a base end of the endoscope and provided with an imaging unit that generates an image by sensing observation light internally with an image sensor, and
the medical observation device is an endoscopic device in which the camera head is supported by the support unit.

(11) A medical observation system, including:
a medical observation device including an imaging unit that captures an image of a surgical site, a vibration sensor that detects a vibration of the imaging unit, a support unit that supports the imaging unit, and a control unit that conducts an image shake correction that corrects a shake in an image captured by the imaging unit, based on a detection value from the vibration sensor; and
a display device that displays an image subjected to the image shake correction by the medical observation device.

(12) An image shake correction method conducted in a medical observation device that includes an observation unit configured to perform magnified observation of a surgical site, a vibration sensor that detects a vibration of the observation unit, and a support unit that supports the observation unit, the image shake correction method including:
conducting an image shake correction that corrects a shake in an image observed by the observation unit, based on a detection value from the vibration sensor.

What is claimed is:

1. A medical observation device, comprising:
an arm that supports a camera; and
circuitry configured to:
determine a vibration characteristic of the camera according to a state of the arm,
on condition that the vibration characteristic is a first vibration characteristic, stabilize an image captured by the camera based on a first control parameter corresponding to the first vibration characteristic, and
on condition that the vibration characteristic is a second vibration characteristic, stabilize an image captured by the camera based on a second control parameter corresponding to the second vibration characteristic and different from the first control parameter.

2. The medical observation device according to claim 1, wherein
the circuitry is configured to determine the vibration characteristic based on a detected user operation of an input device configured to change an operating mode of the arm.

3. The medical observation device according to claim 1, wherein
the vibration characteristic is determined as a mode of vibration accordance with
at least one from among
a footstep vibration produced by a person walking inside an operating room;
a camera movement vibration produced by the camera moving; and
a camera locking vibration produced by the camera being locked at a position after moving.

4. The medical observation device according to claim 1, wherein
the camera includes an imaging device that generates an image by sensing observation light with an image sensor, and
the circuitry is configured to stabilize an image observed by the camera in accordance with an electronic correction method that corrects a shake in an image by correcting a capture position of observation light for each pixel in the image sensor.

5. The medical observation device according to claim 1, wherein
the circuitry is configured to stabilize an image observed by the camera in accordance with an optical correction method using a lens shift technique that corrects a shake in an image by moving a position of an optical system that guides observation light in the camera.

6. The medical observation device according to claim I, wherein
the camera includes an imaging device that generates an image by sensing observation light with an image sensor, and
the circuitry is configured to stabilize the image observed by the camera in accordance with an optical correction method with an imager shift technique that corrects a shake in an image by moving a position of the image sensor.

7. The medical observation device according to claim 1, wherein
the camera includes a housing on which a grip handle is provided.

8. The medical observation device according to claim 1. wherein
the arm includes rotation axis links, and
each of the rotation axis links is provided with a vibration suppression mechanism. that suppresses vibration in the rotation axis link.

9. The medical observation device according to claim 1, wherein
the camera includes an endoscope and a camera head connected to a base end of the endoscope that generates an image by sensing observation light internally with an image sensor, and
the medical observation device is an endoscopic device in which the camera head is supported by the arm.

10. A medical observation system, comprising:
a medical observation device including a camera that captures an image of a surgical site;
an arm that supports the camera;
circuitry configured to:
determine a vivibration characteristic of the camera according to a state of the arm, on condition that the vibration characteristic is a first vibration characteristic, stabilize an image captured by the camera based on a first control parameter correspondin to the first vibration characteristic, and
on condition that the vibration characteristic is a second vibration characteristic, stabilize an image captured by the camera based on a second control parameter corresponding to the second vibration characteristic and different from the first control parameter; and
a display that displays the image stabilized by the circuitry.

11. A method conducted in a medical observation system that includes an arm that supports a camera, the method comprising:
determining a vibration characteristic indicating a vibration characteristic of the camera according to a state of the arm;
on condition that the vibration characteristic is a first vibration characteristic, stabilizing an image captured by the camera based on a first control parameter corresponding to the first vibration characteristic; and
on condition that the vibration characteristic is a second vibration characteristic, stabilizing an image captured by the camera based on a second control parameter corresponding the second vibration characteristic and different from the first control parameter.

12. The medical observation device according to claim 1, further comprising a sensor that detects vibration in a plane parallel to a photosensitive face of the camera.

13. The medical observation system according to claim 10, further comprising a sensor that detects vibration in a plane parallel to a photosensitive face of the camera.

14. The medical observation system according to claim 10, wherein the circuitry is configured to:
wherein
the vibration characteristic is determined in accordance with:
at least one from among a footstep vibration produced by a person walking inside an operating room;
a camera movement vibration produced by the camera moving; and
a camera locking vibration produced by the camera being locked at a position after moving.

15. The method according to claim 11, wherein detecting includes detecting vibration in a plane parallel to a photosensitive face of the camera.

16. The method according to claim 11, further comprising:
wherein
the vibration characteristic is determined in accordance with
at least one from among
a footstep vibration produced by a person walking inside an operating room;
a camera movement vibration produced by the camera moving; and
a camera locking vibration produced by the camera being locked at a position after moving.

* * * * *